United States Patent
Liolios et al.

(10) Patent No.: US 11,771,706 B2
(45) Date of Patent: Oct. 3, 2023

(54) ORAL SOLUTIONS COMPRISING FLUDROCORTISONE ACETATE

(71) Applicant: LABOMED PHARMACEUTICAL COMPANY S.A., Koropi (GR)

(72) Inventors: Georgios Liolios, Chalandri (GR); Tsampikos Dimitrios Panagiotopoulos, Marousi (GR); Konstantinos Pachis, Athens (GR)

(73) Assignee: LABOMED PHARMACEUTICAL COMPANY S.A., Koropi (GR)

( * ) Notice: Subject to any disclaimer, the term of this patent is extended or adjusted under 35 U.S.C. 154(b) by 209 days.

(21) Appl. No.: 17/174,870

(22) Filed: Feb. 12, 2021

(65) Prior Publication Data

US 2021/0260077 A1 Aug. 26, 2021

(30) Foreign Application Priority Data

Feb. 25, 2020 (EP) ..................... 20386012

(51) Int. Cl.
*A61K 31/573* (2006.01)
*A61K 9/00* (2006.01)
*A61K 9/08* (2006.01)
*A61K 47/14* (2017.01)

(52) U.S. Cl.
CPC .......... *A61K 31/573* (2013.01); *A61K 9/0053* (2013.01); *A61K 9/08* (2013.01); *A61K 47/14* (2013.01)

(58) Field of Classification Search
CPC ...... A61K 31/573; A61K 9/0053; A61K 9/08; A61K 47/14
See application file for complete search history.

(56) References Cited

U.S. PATENT DOCUMENTS 6,294,192 B1    9/2001  Patel et al.

FOREIGN PATENT DOCUMENTS

| GB | 2571937 A | * | 9/2019 | ........... A61K 31/573 |
| WO | WO-2007138113 A1 | * | 12/2007 | ......... A61K 31/4745 |
| WO | WO-2009007137 A2 | * | 1/2009 | ............. A61K 31/47 |
| WO | WO-2015174910 A1 | * | 11/2015 | ............. A61K 47/14 |

OTHER PUBLICATIONS

N. Al-Awwadi et al "Challenges in Administration of Corticosteroids for the Treatment of Addison's Disease: A Case Study of Fludrocortisone Acetate", Journal of Bioanalysis & Biomedicine (2017).

S. Cisternino "Stability of Fludrocortisone Acetate Solutions Prepared From Tablets and Powder", European Journal of Pharmaceutics and Biopharmaceutics 55, pp. 209-213 (2003).

* cited by examiner

*Primary Examiner* — Jeffrey S Lundgren
*Assistant Examiner* — Ellie Kwon
(74) *Attorney, Agent, or Firm* — Harness, Dickey & Pierce, P.L.C.

(57) ABSTRACT

Physicochemically stable oral pharmaceutical solution comprising fludrocortisone acetate and a non-aqueous liquid carrier comprising one or more medium-chain fatty acid triglycerides.

13 Claims, No Drawings

ORAL SOLUTIONS COMPRISING FLUDROCORTISONE ACETATE

CROSS-REFERENCE TO RELATED APPLICATIONS

This application claims the benefit and priority of EP20386012.7, filed Feb. 25, 2020. The entire disclosure of the above application is incorporated herein by reference.

FIELD

The present invention relates to oral pharmaceutical solutions comprising as active substance fludrocortisone acetate.

BACKGROUND

Fludrocortisone ((11β)-9-Fluoro-11,17,21-trihydroxypregn-4-ene-3,20-dione) is a well-established active pharmaceutical substance first disclosed in 1953 through U.S. Pat. No. 2,771,475 (Upjohn Co).

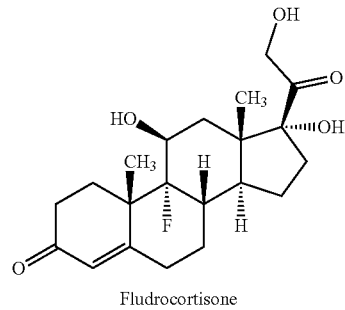

Fludrocortisone

Fludrocortisone is most commonly used in its acetate form.

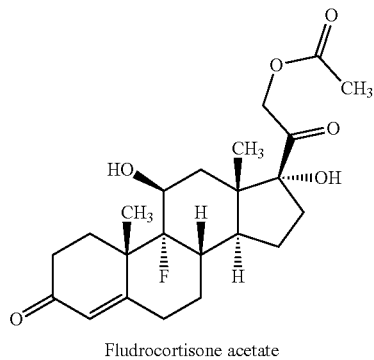

Fludrocortisone acetate

Fludrocortisone acetate is a corticosteroid and exhibits a powerful mineralocorticoid activity along with some additional but comparatively very weak glucocorticoid activity. Relative to cortisol, it is said to have 10 times the glucocorticoid potency but 250 to 800 times the mineralocorticoid potency and it is used to treat adrenogenital syndrome, postural hypotension, and adrenal insufficiency. In case of adrenal insufficiency, it is generally administered along with hydrocortisone.

Fludrocortisone acetate is considered a prodrug as it is hydrolyzed to its active form fludrocortisone when in human organism.

Fludrocortisone acetate is a typical example of a hydrophobic therapeutic agent. Although it is very stable as a solid, in aqueous and alcoholic solutions the a-ketol side chain, as in all such corticosteroids, is prone to oxidative rearrangement and degradation at alkaline pH. It has been reported that hydrocortisone and prednisolone, when exposed to ultraviolet light or ordinary fluorescent laboratory lighting in alcoholic solutions, undergo photolytic degradation of the A-ring. Since fludrocortisone acetate has the same A-ring as hydrocortisone it is also labile under these conditions.

Fludrocortisone acetate is currently formulated only in solid state forms and is commercially available as a 0.1 mg tablet under the brand name Florinef® among others.

Although oral solid dosage forms such as tablets are very popular for reasons that are mainly due to ease of management, for certain users (e.g. children and the elderly) these forms are not necessarily a convenient option, especially due to difficulty in swallowing these forms. This lack of convenience results in high incidence of non-compliance and ineffective therapy.

However, it is apparently extremely challenging to formulate fludrocortisone acetate in the form of a solution for oral administration, since it is an extremely hydrophobic agent.

Cisternino et. al., "*Stability of fludrocortisone acetate solutions prepared from tablets and powder*", European journal of pharmaceutics and biopharmaceutics 55 (2003) 209-213, discloses that fludrocortisone acetate 40 μg/ml oral solutions prepared from tablets and powder show significant degradation of fludrocortisone acetate even when stored at 23° C.

Najim A. AL-Awwadi et. al. "*Challenges in administration of corticosteroids for the treatment of Addison's disease: a case study of fludrocortisone acetate*", J Bioanal Biomed 2017, 9:3, discloses different liquid formulations of fludrocortisone by using various polymers such as poly(ε-caprolactone), Eudragit® RS and Eudragit® RL and different processes such as oil-in-water solvent evaporation methods and suspension-in-oil-in-water evaporation methods. Small poly(ε-caprolactone)-based microparticles were developed during this study, leading to good efficiency when they were prepared as oil-in-water emulsion with 7.5 mg/ml of fludrocortisone.

U.S. Pat. No. 6,294,192 also discloses that another conventional approach to formulating hydrophobic therapeutic agents takes advantage of the increased solubility of hydrophobic therapeutic agents in oils (e.g. triglycerides). Hydrophobic therapeutic agents, while poorly soluble in aqueous solution, could be sufficiently lipophilic that therapeutically effective concentrations of the therapeutic agents can be prepared in triglyceride-based solvents. Thus, one conventional approach is to solubilize a hydrophobic therapeutic agent in a bioacceptable triglyceride solvent, such as a digestible vegetable oil, and disperse this oil phase in an aqueous solution. The dispersion may be stabilized by emulsifying agents and provided in emulsion form. Alternatively, the therapeutic agent can be provided in water-free formulations.

However, according to U.S. Pat. No. 6,294,192, although triglyceride-based pharmaceutical compositions are useful in solubilizing and delivering some hydrophobic therapeutic agents, such compositions are subject to a number of significant limitations and disadvantages. For example emulsions are thermodynamically unstable, and colloidal emulsion particles will spontaneously agglomerate, eventually leading to complete phase separation.

The present invention overcomes the problems of the prior art and provides an oral pharmaceutical solution, comprising fludrocortisone acetate, which exhibits excellent stability and extended lifetime.

SUMMARY

The present invention provides a physicochemically stable oral pharmaceutical solution comprising fludrocortisone acetate.

The oral pharmaceutical solution according to the invention comprises fludrocortisone acetate and a non-aqueous liquid carrier comprising one or more medium-chain fatty acid triglycerides.

The oral pharmaceutical solution according to the invention presents excellent physicochemical stability.

The present invention has the advantage that it provides a stable oral pharmaceutical solution of fludrocortisone acetate, by inhibiting hydrolysis and oxidation that typically occur after extended storage.

Preferably, the oral pharmaceutical solution according to the invention is free from ethanol, propylene glycol, polyethylene glycol, sorbitol, glycerol, maltitol, polyvinylpyrrolidone, copolyvidone, sorbitan monolaurate, propylene glycol monolaurate (lauroglycol), carboxymethyl cellulose and microcrystalline cellulose mixtures, as well as free from lipophilic surfactants such as polysorbate 80, polyethylene glycol, castor oils and polyethylene glycol hydrogenated castor oils.

Further areas of applicability will become apparent from the description provided herein. The description and specific examples in this summary are intended for purposes of illustration only and are not intended to limit the scope of the present disclosure.

DETAILED DESCRIPTION

Example embodiments will now be described more fully with reference to the accompanying drawings.

The present invention provides an oral pharmaceutical solution comprising fludrocortisone acetate, in association with a pharmaceutically acceptable non-aqueous liquid carrier.

The term "% w/v" refers to g of the respective substance per 100 ml of the oral solution.

As used throughout the present description and claims, the term "non-aqueous" means essentially water-free.

As used throughout the present description and claims, the term "total impurities" refers to the sum of all fludrocortisone acetate degradation impurities present in the oral solution, except for fludrocortisone.

The term "stable" as used herein, refers to both physical and chemical stability, wherein no more than 1.2% w/w of fludrocortisone and no more than 1.5% w/w of total impurities are formed on storage at 40° C. and 75% relative humidity over a period of three months.

The desire for the development of an oral solution of fludrocortisone acetate is complicated by the fact that the molecule is susceptible to hydrolysis and degrades significantly especially at alkaline and oxidative conditions. Although fludrocortisone acetate is very soluble in lipids and triglycerides, the physicochemical stability of fludrocortisone acetate oily solutions has not been addressed in the prior art.

There are numerous lipids comprising triglycerides of fatty acids commercially available to formulators as excipients for lipid-based drug delivery systems. Many synthetic lipids are also available in which the glycerol backbone has been replaced by propylene glycol and/or polyethylene glycols. Additionally, the degree of esterification of the fatty acid moiety may vary, forming mono-, di- and tri-glycerides as well as different esters of propylene glycol and polyethylene glycols. The fatty acids are not necessarily long chain ($C_{11}$-$C_{22}$); they can be medium-chain ($C_6$-$C_{10}$), short chain, unsaturated or branched. Due to these differences in chemical nature, there are numerous lipids or lipid-like excipients available commercially, all of which are colloquially called 'lipids' in the pharmaceutical field.

The term "medium-chain triglycerides" according to the present invention refers to triglycerides of saturated fatty acids having an aliphatic chain of 6 to 10 carbon atoms ($C_{6:0}$ to $C_{10:0}$).

Unexpectedly, it has been found that the inclusion of many mixed mono-, di- and tri-glycerides, such as glycerol monocaprylocarpate (i.e. medium chain monoglyceride (60% w/w) and diglyceride (35% w/w) consisting of 83% w/w caprylic acid and 17% w/w capric acid) and glycerol dicaprylate (i.e. medium chain diglyceride (83% w/w) comprising 75%-85% w/w caprylic acid) to oral solutions comprising fludrocortisone acetate did not actually enhance the stability of fludrocortisone acetate.

It has been further found that many lipophilic surfactants, commonly used in drug carrier systems such as polysorbate 80, polyethylene glycol castor oils and polyethylene glycol hydrogenated castor oils are also ineffective to slow down the decomposition of the active agent after storage.

On the other hand, it has now been found that the physicochemical stability of fludrocortisone acetate is considerably enhanced in non-aqueous liquid carriers comprising one or more medium-chain fatty acid triglycerides. This finding is unexpected since it does not apply to other triglycerides, such as long chain triglycerides. For example, the addition of corn oil, sunflower oil or castor oil does not enhance the stability of fludrocortisone acetate in a non-aqueous solution.

The oral pharmaceutical solution according to the invention comprises fludrocortisone acetate and a non-aqueous liquid carrier comprising one or more medium-chain fatty acid triglycerides.

Preferably, the oral pharmaceutical solution according to the invention comprises from 0.001% w/v to 0.01% w/v fludrocortisone acetate.

More preferably, the oral pharmaceutical solution according to the invention comprises from 0.002% w/v to 0.005% w/v fludrocortisone acetate.

The European Pharmacopoeia (Ph. Eur. 6.0) describes medium-chain triglycerides as the fixed oil extracted from the hard, dried fraction of the endosperm of *Cocos nucifera* L. or from the dried endosperm of *Elaeis guineenis* Jacq. They comprise a mixture of triglycerides of saturated fatty acids, mainly of caprylic acid ($C_{8:0}$) and of capric acid ($C_{10:0}$). They contain no less than 95% w/w of saturated fatty acids (expressed as percent (%) by weight of total mixture).

According to Handbook of excipients, sixth edition (2009), medium-chain triglycerides (synonyms; MCT oil, caprylic/capric triglyceride, glyceryl tricaprylate/caprate) may also be known as fractionated coconut oil, which contains three saturated lipid chains bound to a glycerin backbone, and are distinguished from other triglycerides by the length of the carbon chains, normally between 6 and 10.

Medium chain triglycerides have been used in a variety of pharmaceutical formulations including oral, parenteral and topical preparations mainly as emulsifying agents or solvents. They are usually colorless to slightly yellow liquids that are practically odorless and tasteless, while they solidify at about 0° C.

According to a preferred embodiment, the medium-chain triglyceride according to the invention is caprylic acid triglyceride.

According to another preferred embodiment, the medium-chain triglyceride according to the invention is a mixture of caprylic acid and capric acid triglycerides. Preferably the medium-chain triglyceride according to the invention is a mixture of caprylic acid and capric acid triglycerides in a weight ratio caprylic acid:capric acid from 4:6 to 99:1. More preferably the medium-chain triglyceride according to the invention is a mixture of caprylic acid and capric acid triglycerides in a weight ratio caprylic acid:capric acid from 4.5:5.5 to 95:5. Even more preferably the medium-chain triglyceride according to the invention is a mixture of caprylic acid and capric acid triglycerides in a weight ratio caprylic acid:capric acid from 5:5 to 90:10.

Preferably the medium-chain triglyceride according to the invention has a saponification value from 320 to 380 mg KOH/g. More preferably the medium-chain triglyceride according to the invention has a saponification value from 330 to 370 mg KOH/g. Even more preferably the medium-chain triglyceride according to the invention has a saponification value from 335 to 365 mg KOH/g.

Preferable examples of medium-chain triglycerides according to the invention include caprylic triglyceride with fatty-acid composition of about 99% w/w caprylic acid ($C_{8:0}$) (synonyms: tricaprylin, glycerol trioctanoate), with a saponification value of 335 to 360 mg KOH/g e.g. Captex® 8000, which is a synthetic triglyceride manufactured by esterification of caprylic acid and glycerin.

caprylic/capric triglyceride with fatty-acid composition of 65% to 80% w/w caprylic acid ($C_{8:0}$), 20% to 35% w/w capric acid, less than 2% w/w caproic acid ($C_{6:0}$), less than 2% w/w lauric acid ($C_{12:0}$) and less than 1% w/w myristic acid ($C_{14:0}$), with a saponification value of 335 to 355 mg KOH/g e.g. Miglyol® 810, BergaBest® MCT Oil 70/30 & Captex® 300.

caprylic/capric triglyceride with fatty-acid composition of 55% to 70% w/w caprylic acid ($C_{8:0}$) & 30% to 45% w/w capric acid ($C_{10:0}$), with a saponification value of 330 to 360 mg KOH/g. e.g. Neobee® M-5, Cromadol GTCC & Myritol® 318.

caprylic/capric triglyceride with fatty-acid composition of 50 to 65% caprylic acid ($C_{8:0}$), 30% to 45% w/w capric acid ($C_{10:0}$), less than 2% w/w caproic acid ($C_{6:0}$), less than 2% w/w lauric acid ($C_{12:0}$) and less than 1% w/w myristic acid ($C_{14:0}$), with a saponification value of 325 to 345 mg KOH/g e.g. Miglyol® 812, BergaBest® MCT Oil 60/40 & Captex® 355.

The total concentration of the medium-chain triglycerides in the oral pharmaceutical solution according to the invention is at least 45% w/v. Preferably the total concentration of the medium-chain triglycerides is at least 60% w/v. Even more preferably the total concentration of the medium-chain triglycerides is at least 90% w/v. Even more preferably the total concentration of the medium-chain triglycerides is at least 95% w/v.

Preferably, the oral pharmaceutical solution according to the invention is free from ethanol, propylene glycol, polyethylene glycol, sorbitol, glycerol, maltitol, polyvinylpyrrolidone, copolyvidone, sorbitan monolaurate, propylene glycol monolaurate (lauroglycol), carboxymethyl cellulose and microcrystalline cellulose mixtures, as well as free from lipophilic surfactants such as polysorbate 80, polyethylene glycol castor oils and polyethylene glycol hydrogenated castor oils.

Preferably, the oral pharmaceutical solution according to the invention is free from any stabilizing agent which is not a medium chain triglyceride.

The oral pharmaceutical solution, according to the invention may also comprise additional excipients commonly used in preparing oral liquid compositions, such as antimicrobial preservatives, antioxidants, sweeteners and flavouring agents.

Antimicrobial preservatives may include but are not limited to sodium benzoate, benzoic acid, boric acid, sorbic acid and their salts thereof, benzyl alcohol, parahydroxybenzoic acids and their alkyl esters, methyl, ethyl and propyl parahydroxybenzoates and their salts or mixtures thereof.

Antioxidants which may be used in the present invention comprise, amongst others, butylated hydroxytoluene, butylated hydroxyanisole, ethylenediamine tetraacetic acid ("EDTA"), ascorbic acid, sodium metabisulfite and propyl gallate or any combinations thereof.

Sweeteners may include but are not limited to aspartame, acesulfame potassium, thaumatin, saccharin and salts thereof, sodium cyclamate, glycyrrhizin, monosodium glycyrrhizinate, monoamonium glycyrrhizinate or mixtures thereof.

The oral pharmaceutical solution, according to the invention may further comprise flavours and/or colours so as to enhance its palatability and/or visual appearance. Suitable flavouring agents and colouring agents are well known to those skilled in the art. The flavouring agent may be a natural or artificial flavouring agent, including an essence, an extract, a flavour oil or combinations thereof. Exemplary flavours include, but are not limited to: honey flavour, raspberry flavour, strawberry flavour, blueberry flavour, blackberry flavour, grape flavour, peach flavour, apricot flavour, watermelon flavour, melon flavour, fruit punch flavour, cranberry flavour, mango flavour, banana flavour, citrus flavour, orange flavour, lemon flavour, grapefruit flavour, cherry flavour, vanilla flavour, caramel flavour, chocolate flavour, marshmallow flavour, coffee flavour and coconut flavour.

The oral pharmaceutical solution according to the invention is preferably supplied as multidose preparation. Each dose from a multidose container may be administered by means of a device suitable for accurately measuring the prescribed volume. The device is usually a spoon or a cup for volumes of 5 mL or multiples thereof, or an oral syringe for other volumes. Preferably, the device is an oral syringe.

The oral pharmaceutical solution of the present invention may be prepared using methods well known in the art and using regular manufacturing equipment.

For example, it may be prepared using the following process: The active substance and the excipients are weighed. The selected medium-chain triglyceride(s) is added into a vessel and heated to 30-35° C. Fludrocortisone acetate is added into the vessel under stirring until it totally dissolves. The remaining excipients, if present, are successively added under continuous stirring, until complete dissolution. Finally, the volume is adjusted with a quantity of the medium-chain triglyceride(s).

The final solution is optionally filtered over a 10 μm filter, and filled preferably in light-protective containers, such as amber type III glass 50 or 100 mL bottles sealed with child resistant, tamper evident screw caps.

EXAMPLES

Example 1

Aqueous liquid compositions of fludrocortisone acetate.

These fludrocortisone acetate compositions were prepared in the following manner: A quantity of purified water was added into a vessel. Fludrocortisone acetate and the cosolvent were successively dissolved into purified water. A pH buffer solution, prepared in a different vessel, was added, under continuous stirring, until fludrocortisone acetate was completely dissolved. The remaining excipients, were successively added under continuous stirring, until complete dissolution. The pH of the solution was adjusted to the desired value. Finally, the volume was adjusted with purified water.

TABLE 1

| Component | Function | Trial 1 (pH~3.5) | Trial 2 (pH~4.0) | Trial 3 (pH~3.0) |
|---|---|---|---|---|
| | | mg/ml | | |
| Fludrocortisone acetate | API | 0.02 | 0.02 | 0.02 |
| Citric acid monohydrate | Buffering agent | 3.0 | 3.0 | |
| Sodium Citrate dihydrate | Buffering agent | 1.0 | 1.5 | |
| Hydrochloric acid | Acidifying agent | — | — | q.s. to pH = 3 |
| Propylene glycol | Co-solvent | 150 | 150 | 150 |
| Sorbitol 70% | Sweetener | 300 | 300 | 300 |
| Diluent | Purified water | | Qs to 1 mL | |

Storage conditions of temperature (40° C.) and relative humidity (75%) applied for a period of three months. Quantification of fludrocortisone acetate and its degradation impurities was performed by HPLC.

TABLE 1a

| | Trial 1 | | |
|---|---|---|---|
| | Time points/Conditions | | |
| | | 40° C. ± 2° C., 75% RH | |
| Controls | T = 0 | T = 2 months | T = 3 months |
| Appearance | Clear colorless solution | Clear colorless solution | Clear colorless solution |
| Assay fludro/sone acetate | 104.6% | 96.1% | 86.8% |
| Impurities | Fludro/sone: 1.9% Total: 0.1% | Fludro/sone: 9.8% Total: 1.4% | Fludro/sone: 15.3% Total: 2.1% |
| pH | 3.6 | 3.6 | 3.6 |

TABLE 1b

| | Trial 2 | | |
|---|---|---|---|
| | Time points/Conditions | | |
| | | 40° C. ± 2° C., 75% RH | |
| Controls | T = 0 | T = 2 months | T = 3 months |
| Appearance | Clear colorless solution | Clear colorless solution | Clear colorless solution |
| Assay fludro/sone acetate | 104.2% | 98.9% | 90.9% |
| Impurities | Fludro/sone: 1.1% Total: 0.1% | Fludro/sone: 5.5% Total: 2.0% | Fludro/sone: 8.6% Total: 3.3% |
| pH | 4.0 | 4.1 | 4.1 |

TABLE 1c

| | Trial 3 | | |
|---|---|---|---|
| | Time points/Conditions | | |
| | | 40° C. ± 2° C., 75% RH | |
| Controls | T = 0 | T = 2 months | T = 3 months |
| Appearance | Clear colorless solution | Clear colorless solution | Clear colorless solution |
| Assay fludro/sone acetate | 101.9% | 92.3% | 81.0% |
| Impurities | Fludro/sone: 2.5% Total: 0.1% | Fludro/sone: 11.6% Total: 1.4% | Fludro/sone: 17.8% Total: 2.3% |
| pH | 3.5 | 3.6 | 3.6 |

According to the above results, fludrocortisone acetate is unstable and easily hydrolyzed to its active form (fludrocortisone) as the assay value decreases as time passes by and the levels of fludrocortisone increase.

Example 2

Aqueous liquid suspension (Trial 1) vs aqueous solutions (Trial 2, Trial 3) of fludrocortisone acetate.

The fludrocortisone acetate aqueous suspension was prepared in the following manner:

A quantity of purified water was added into a vessel. The suspending agent, the cosolvent(s) and fludrocortisone acetate were successively added into the vessel under stirring. A pH buffer solution, prepared in a different vessel, was added, under continuous stirring, into the vessel. The remaining excipients were successively added, into the vessel. The pH of the solution was adjusted to the desired value. Finally, the volume was adjusted with purified water.

The fludrocortisone acetate aqueous solution were prepared in the following manner:

A quantity of purified water was added into a vessel. Fludrocortisone acetate and the cosolvent(s), were successively dissolved into purified water under stirring. A pH buffer solution, prepared in a different vessel, was added, under continuous stirring, until fludrocortisone acetate was completely dissolved. The remaining excipients, were successively added under continuous stirring, until complete dissolution. The pH of the solution was adjusted to the desired value. Finally, the volume was adjusted with purified water.

TABLE 2a

| Component | Function | Trial 1 (suspension) mg/ml | Trial 2 mg/ml | Trial 3 mg/ml |
|---|---|---|---|---|
| Fludrocortisone acetate | API | 0.1 | 0.02 | 0.02 |
| Sodium benzoate | Anti-microbial agent | 1.0 | 1.0 | 1.0 |
| Citric acid monohydrate | Buffering agent | 6.0 | 6.0 | 6.0 |
| Sodium citrate dihydrate | | 3.0 | 3.0 | 3.0 |
| Propylene glycol | Co-solvent | — | 150 | 100 |
| Glycerol | Co-solvent | 530 | 250 | 120 |
| Polyethylenge glycol 1450 | Co-solvent | — | 150 | — |
| Maltitol | Sweetener | 630 | — | — |
| Sorbitol | Sweetener | — | 400 | — |
| Polysorbate 80 | Co-solvent | 1.5 | — | — |
| Carboxymethyl cellulose/ microcrystalline cellulose (MCC/CMC P591) | Suspending agent | 10 | — | — |
| Sucrose | Sweetener | — | — | 680 |
| Acetic acid (10%)/ Sodium acetate (10%) | pH adjusting agent | q.s. to pH 4.5 | | |
| Purified water | Diluent | q.s to 1 ml | | |

Storage conditions of temperature (40° C.) and relative humidity (75%) applied for a period of three months. Quantification of fludrocortisone acetate and its degradation impurities was performed by HPLC.

TABLE 2b

| | 40° C. ± 2° C., 75% RH | |
|---|---|---|
| | T = 1 month | T = 2 months |
| Trial 1 (suspension) | Fludro/sone: 4.9% Total: 3.1% | Fludro/sone: 8.3% Total: 3.7% |
| Trial 2 | Fludro/sone: 3.2% Total: 1.4% | Fludro/sone: 5.2% Total: 2.7% |
| Trial 3 | Fludro/sone: 4.3% Total: 2.5% | Fludro/sone: 7.4% Total: 3.2% |

According to the above results, the fludrocortisone suspension presents a similar degradation profile as the clear solutions.

Example 3

Non-aqueous liquid compositions of fludrocortisone acetate.

These fludrocortisone acetate solutions were prepared in the following manner:

Approximately 80% of the total quantity of the selected medium-chain triglyceride was added into a vessel and heated to 30-35° C. Fludrocortisone acetate was added into the vessel under stirring until totally dissolving. The selected oils or glyceride mixtures were then added under continuous stirring. Finally, the volume was adjusted with the required quantity of the above medium-chain triglyceride and/or the oils or glyceride mixtures.

TABLE 3a

| | Composition % w/v | | | | | |
|---|---|---|---|---|---|---|
| | Ia | IIa | IIIa | IVa | Va | VIa |
| Active substance | | | | | | |
| Fludrocortisone acetate | 0.004 | 0.004 | 0.004 | 0.004 | 0.004 | 0.004 |
| Excipients | | | | | | |
| Miglyol 812 ® (50 to 65% ($C_{8:0}$)/ 30% to 45% ($C_{10:0}$) triglyceride) | 99.996 | 49.998 | 89.9964 | — | — | — |
| Corn oil | — | 49.998 | — | — | — | — |
| Sunflower oil | — | — | 9.9996 | — | — | — |
| Castor oil | — | — | — | 99.996 | — | — |
| Glycerol dicaprylate | — | — | — | — | 99.996 | — |
| Glycerol mono-caprylocarpate (Capmul MCM ®) | — | — | — | — | — | 99.996 |

Storage conditions of temperature (40° C.) and relative humidity (75%) applied for a period of two months. Quantification of fludrocortisone acetate and its degradation impurities was performed by HPLC.

TABLE 3b

| | 40° C. ± 2° C., 75% RH | |
|---|---|---|
| | T = 0 | T = 2 months |
| Trial Ia | Fludro/sone: 0.1% Total: 0.1% | Fludro/sone: 0.1% Total: 0.6% |
| Trial IIa | Fludro/sone: 0.1% Total: 0.2% | Fludro/sone: 0.3% Total: 0.9% |
| Trial IIIa | Fludro/sone: 0.2% Total: 0.2% | Fludro/sone: 0.2% Total: 1.3% |
| Trial IVa | Fludro/sone: 0.1% Total: 0.1% | Fludro/sone: 2.2% Total: 1.9% |
| Trial Va | Fludro/sone: 0.1% Total: 0.2% | Fludro/sone: 3.4% Total: 1.2% |
| Trial VIa | Fludro/sone: 0.1% Total: 0.1% | Fludro/sone: 4.4% Total: 2.1% |

Example 4

Table IV shows preferred oral solution compositions according to the present invention.

These fludrocortisone acetate solutions were prepared in the following manner:

The active substance and the excipients were weighed. Approximately 80% of the total quantity of the selected medium-chain triglyceride(s) was added into a vessel and heated to 30-35° C. Fludrocortisone acetate was added into the vessel under stirring until totally dissolving. The flavour was then added under continuous stirring, until complete dissolution. Finally, the volume was adjusted with the required quantity of the above medium-chain triglyceride(s).

TABLE 4a preferred oral solution compositions
according to the present invention

| | Composition | | | |
|---|---|---|---|---|
| | I | II | III | IV |
| | | % w/v | | |
| Active substance | | | | |
| Fludrocortisone acetate | 0.004 | 0.004 | 0.004 | 0.004 |
| Excipients | | | | |
| Miglyol 812 ® (50 to 65% ($C_{8:0}$)/30% to 45% ($C_{10:0}$) triglyceride) | 99.796 | 49.898 | — | 49.898 |
| Miglyol 810 ® (65 to 80% ($C_{8:0}$)/20% to 35% ($C_{10:0}$) triglyceride) | — | 49.898 | 99.796 | 49.898 |
| Tutti frutti flavour | 0.2 | 0.2 | 0.2 | 0.2 |

Storage conditions of temperature (40° C.) and relative humidity (75%) applied for a period of three months. Quantification of fludrocortisone acetate and its degradation impurities was performed by HPLC.

TABLE 4b

Stability results

| | Composition I | Composition II | Composition III | Composition IV |
|---|---|---|---|---|
| Appearance (T = 0) | Clear oily solution | Clear oily solution | Clear oily solution | Clear oily solution |
| Assay (T = 0) | 100.9% | 100.2% | 98.9% | 99.3% |
| Fludrocortisone (T = 0) | 0.1% | 0.1% | 0.1% | 0.2% |
| Total impurities (T = 0) | 0.1% | 0.1% | 0.2% | 0.1% |
| Appearance (T = 3 m) | Clear oily solution | Clear oily solution | Clear oily solution | Clear oily solution |
| Assay (T = 3 m) | 100.6% | 100.1% | 99.0% | 99.0% |
| Fludro/sone (T = 3 m) | 0.2% | 0.2% | 0.4% | 0.3% |
| Total impurities (T = 3 m) | 0.5% | 0.7% | 0.4% | 0.4% |

Example 5

Table V shows preferred oral solution compositions according to the present invention. These fludrocortisone acetate solutions were prepared as described in previous Example 4.

TABLE 5a preferred oral solution compositions
according to the present invention

| | Composition | | | |
|---|---|---|---|---|
| | V | VI | VII | VIII |
| | | % w/v | | |
| Active substance | | | | |
| Fludrocortisone acetate | 0.004 | 0.004 | 0.004 | 0.004 |
| Excipients | | | | |
| Captex 8000 ® (~99% ($C_{8:0}$) triglyceride) | 99.796 | 49.898 | — | 49.898 |
| Captex 355 ® (50% to 65% ($C_{8:0}$)/30% to 45% ($C_{10:0}$) triglyceride) | — | 49.898 | 99.796 | 49.898 |
| Tutti frutti flavour | 0.2 | 0.2 | 0.2 | 0.2 |

Storage conditions of temperature (40° C.) and relative humidity (75%) applied for a period of three months. Quantification of fludrocortisone acetate and its degradation impurities, in the compositions prepared, was performed by HPLC.

TABLE 5b

Stability results

| | Composition I | Composition II | Composition III | Composition IV |
|---|---|---|---|---|
| Appearance (T = 0) | Clear oily solution | Clear oily solution | Clear oily solution | Clear oily solution |
| Assay (T = 0) | 100.3% | 99.2% | 99.9% | 99.0% |
| Fludrocortisone (T = 0) | 0.1% | 0.2% | 0.1% | 0.2% |
| Total impurities (T = 0) | 0.1% | 0.2% | 0.2% | 0.1% |
| Appearance (T = 3 m) | Clear oily solution | Clear oily solution | Clear oily solution | Clear oily solution |
| Assay (T = 3 m) | 98.6% | 98.7% | 99.0% | 98.1% |
| Fludro/sone (T = 3 m) | 0.4% | 0.3% | 0.4% | 0.4% |
| Total impurities (T = 3 m) | 1.1% | 0.6% | 0.3% | 0.4% |

What is claimed is:

1. Oral pharmaceutical solution comprising from 0.001% w/v to 0.01% w/v fludrocortisone acetate and a non-aqueous liquid carrier comprising one or more triglycerides of saturated fatty acids having an aliphatic chain of 6 to 10 carbon atoms (medium-chain triglycerides), wherein the total concentration of medium-chain triglycerides in the oral solution is at least 60% w/v.

2. Oral pharmaceutical solution according to claim 1, comprising 0.002% w/v to 0.005% w/v fludrocortisone acetate.

3. Oral pharmaceutical solution according to claim 1, wherein the total concentration of medium-chain triglycerides in the oral solution is at least 90% w/v.

4. Oral pharmaceutical solution according to claim 1, wherein the total concentration of medium-chain triglycerides in the oral solution is at least 95% w/v.

5. Oral pharmaceutical solution according to claim 1, wherein the medium-chain triglyceride is caprylic acid triglyceride.

6. Oral pharmaceutical solution according to claim 1, wherein the one or more medium-chain triglycerides is a mixture of caprylic acid and capric acid triglycerides in a weight ratio caprylic acid:capric acid from 4:6 to 99:1.

7. Oral pharmaceutical solution according to claim 1, wherein the one or more medium-chain triglycerides is a mixture of caprylic acid and capric acid triglycerides in a weight ratio caprylic acid:capric acid from 4.5:5.5 to 95:5.

8. Oral pharmaceutical solution according to claim 1, wherein the one or more medium-chain triglycerides is a mixture of caprylic acid and capric acid triglycerides in a weight ratio caprylic acid:capric acid from 5:5 to 90:10.

9. Oral pharmaceutical solution according to claim 1, wherein the one or more medium-chain triglycerides have a saponification value from 320 to 380 mg KOH/g.

10. Oral pharmaceutical solution according to claim 1, wherein the one or more medium-chain triglycerides have a saponification value from 330 to 370 mg KOH/g.

11. Oral pharmaceutical solution according to claim 1, wherein the one or more medium-chain triglycerides have a saponification value from 335 to 365 mg KOH/g.

12. Oral pharmaceutical solution according to claim 1, wherein the solution is free from ethanol, propylene glycol, polyethylene glycol, sorbitol, glycerol, maltitol, polyvinylpyrrolidone, copolyvidone, sorbitan monolaurate, propylene glycol monolaurate (lauroglycol), carboxymethyl cellulose and microcrystalline cellulose mixtures, and lipophilic surfactants.

13. Oral pharmaceutical solution according to claim 1, wherein the solution is free from any stabilizing agent which is not a medium chain triglyceride.

* * * * *